(12) United States Patent
Young et al.

(10) Patent No.: US 8,402,151 B2
(45) Date of Patent: Mar. 19, 2013

(54) DYNAMIC COMMUNICATION STACK

(75) Inventors: Morris J. Young, Indianapolis, IN (US); David Bradley Markisohn, Indianapolis, IN (US); Christopher Spieth, Sheridan, IN (US); Allen B. Cummings, Westfield, IN (US); Adam R. Scroggin, Noblesville, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 957 days.

(21) Appl. No.: 11/999,934

(22) Filed: Dec. 7, 2007

(65) Prior Publication Data
US 2009/0150549 A1 Jun. 11, 2009

(51) Int. Cl.
G06F 15/16 (2006.01)
G06F 3/00 (2006.01)
G06F 13/00 (2006.01)

(52) U.S. Cl. ............ 709/230; 709/227; 709/228; 710/1; 710/5; 710/8; 710/11; 719/328; 719/329

(58) Field of Classification Search .................. 709/217, 709/208–211, 227–230, 236, 237, 248; 607/60; 370/310; 710/1, 5, 8, 11; 719/328, 329
See application file for complete search history.

(56) References Cited

U.S. PATENT DOCUMENTS

| | | | |
|---|---|---|---|
| 4,731,726 A | 3/1988 | Allen, III | |
| 5,251,126 A | 10/1993 | Kahn et al. | |
| 5,302,947 A * | 4/1994 | Fuller et al. | 340/5.42 |
| 5,338,157 A | 8/1994 | Blomquist | |
| 5,376,070 A | 12/1994 | Purvis et al. | |
| 5,658,250 A | 8/1997 | Blomquist et al. | |
| 5,665,065 A | 9/1997 | Colman et al. | |
| 5,795,327 A | 8/1998 | Wilson et al. | |
| 5,826,027 A * | 10/1998 | Pedersen et al. | 709/221 |
| 5,903,754 A * | 5/1999 | Pearson | 719/310 |
| 5,954,641 A | 9/1999 | Kehr et al. | |
| 6,024,699 A | 2/2000 | Surwit et al. | |
| 6,068,615 A | 5/2000 | Brown et al. | |
| 6,102,855 A | 8/2000 | Kehr et al. | |
| 6,110,148 A | 8/2000 | Brown et al. | |

(Continued)

FOREIGN PATENT DOCUMENTS

| | | |
|---|---|---|
| EP | 0 699 046 | 9/1996 |
| EP | 0 970 655 | 1/2000 |

(Continued)

OTHER PUBLICATIONS

"Getting Started, CareLink Personal Therapy Management Software for Diabetes," Brochure, 2007, 20pp., Medtronic Minimed, Inc.*

(Continued)

Primary Examiner — Tae Kim
(74) Attorney, Agent, or Firm — Faegre Baker Daniels (57) ABSTRACT

A method of facilitating communication between a resource and a computer is described. The computer employs a software application that allows the computer to communicate with the resource. The resource may comprise a medical device such as a blood glucose meter or an insulin pump. In order to facilitate communication between the computer and the resource, the software constructs a communication protocol particular to the type of resource connected to the computer. The stack comprising the communication protocol allows the computer to communicate with the resource. Once the resource and computer cease communication, the stack may be removed from the memory of the computer.

26 Claims, 2 Drawing Sheets

U.S. PATENT DOCUMENTS

| | | | |
|---|---|---|---|
| 6,113,578 A | 9/2000 | Brown | |
| 6,241,704 B1 | 6/2001 | Peterson et al. | |
| 6,249,809 B1* | 6/2001 | Bro | 709/217 |
| 6,314,405 B1 | 11/2001 | Richardson | |
| 6,322,502 B1 | 11/2001 | Schoenberg et al. | |
| 6,368,272 B1 | 4/2002 | Porumbescu | |
| 6,416,471 B1* | 7/2002 | Kumar et al. | 600/300 |
| 6,427,088 B1 | 7/2002 | Bowman, IV et al. | |
| 6,544,212 B2 | 4/2003 | Galley et al. | |
| 6,551,276 B1 | 4/2003 | Mann et al. | |
| 6,558,320 B1 | 5/2003 | Causey, III et al. | |
| 6,562,001 B2 | 5/2003 | Lebel et al. | |
| 6,564,105 B2 | 5/2003 | Starkweather et al. | |
| 6,571,128 B2 | 5/2003 | Lebel et al. | |
| 6,577,899 B2 | 6/2003 | Lebel et al. | |
| 6,585,644 B2 | 7/2003 | Lebel et al. | |
| 6,605,038 B1 | 8/2003 | Teller et al. | |
| 6,635,014 B2 | 10/2003 | Starkweather et al. | |
| 6,648,821 B2 | 11/2003 | Lebel et al. | |
| 6,659,948 B2 | 12/2003 | Lebel et al. | |
| 6,668,196 B1 | 12/2003 | Villegas et al. | |
| 6,687,546 B2 | 2/2004 | Lebel et al. | |
| 6,694,191 B2 | 2/2004 | Starkweather et al. | |
| 6,714,724 B1 | 3/2004 | Cook | |
| 6,733,446 B2 | 5/2004 | Lebel et al. | |
| 6,740,075 B2 | 5/2004 | Lebel et al. | |
| 6,752,787 B1 | 6/2004 | Causey, III et al. | |
| 6,758,810 B2 | 7/2004 | Lebel et al. | |
| 6,781,522 B2 | 8/2004 | Sleva et al. | |
| 6,804,656 B1 | 10/2004 | Rosenfeld et al. | |
| 6,809,653 B1 | 10/2004 | Mann et al. | |
| 6,810,290 B2 | 10/2004 | Lebel et al. | |
| 6,811,533 B2 | 11/2004 | Lebel et al. | |
| 6,811,534 B2 | 11/2004 | Bowman, IV et al. | |
| 6,813,519 B2 | 11/2004 | Lebel et al. | |
| 6,852,104 B2 | 2/2005 | Blomquist | |
| 6,873,268 B2 | 3/2005 | Lebel et al. | |
| 6,958,705 B2 | 10/2005 | Lebel et al. | |
| 6,988,142 B2* | 1/2006 | Molnar | 709/230 |
| 6,996,833 B1* | 2/2006 | Olson et al. | 719/332 |
| 7,020,508 B2 | 3/2006 | Stivoric et al. | |
| 7,024,236 B2 | 4/2006 | Ford et al. | |
| 7,029,455 B2 | 4/2006 | Flaherty | |
| 7,039,703 B1 | 5/2006 | Clancy et al. | |
| 7,041,468 B2 | 5/2006 | Drucker et al. | |
| 7,063,665 B2 | 6/2006 | Hasegawa et al. | |
| 7,072,356 B1 | 7/2006 | Clancy et al. | |
| 7,076,572 B1* | 7/2006 | Siraj | 710/11 |
| 7,082,334 B2 | 7/2006 | Boute et al. | |
| 7,110,836 B2* | 9/2006 | Sturm et al. | 700/83 |
| 7,120,488 B2 | 10/2006 | Nova et al. | |
| 7,165,062 B2 | 1/2007 | O'Rourke | |
| 7,179,226 B2 | 2/2007 | Crothall et al. | |
| 7,181,350 B2 | 2/2007 | Oberding et al. | |
| 7,523,237 B2* | 4/2009 | Gerig | 710/105 |
| 7,730,499 B2* | 6/2010 | Olson et al. | 719/328 |
| 7,945,897 B1* | 5/2011 | Cook | 717/121 |
| 2002/0016568 A1 | 2/2002 | Lebel et al. | |
| 2002/0029776 A1 | 3/2002 | Blomquist | |
| 2002/0040208 A1 | 4/2002 | Flaherty et al. | |
| 2002/0082665 A1* | 6/2002 | Haller et al. | 607/60 |
| 2002/0193679 A1 | 12/2002 | Malave et al. | |
| 2003/0004403 A1* | 1/2003 | Drinan et al. | 600/301 |
| 2003/0011646 A1 | 1/2003 | Levine et al. | |
| 2003/0060765 A1 | 3/2003 | Campbell et al. | |
| 2003/0065308 A1 | 4/2003 | Lebel et al. | |
| 2003/0065536 A1 | 4/2003 | Hansen et al. | |
| 2003/0078036 A1* | 4/2003 | Chang et al. | 455/419 |
| 2003/0163088 A1 | 8/2003 | Blomquist | |
| 2003/0163789 A1 | 8/2003 | Blomquist | |
| 2004/0003389 A1* | 1/2004 | Reynar et al. | 717/178 |
| 2004/0073464 A1 | 4/2004 | Huang | |
| 2004/0119742 A1 | 6/2004 | Silbey et al. | |
| 2004/0127958 A1* | 7/2004 | Mazar et al. | 607/60 |
| 2004/0172284 A1 | 9/2004 | Sullivan et al. | |
| 2004/0235446 A1 | 11/2004 | Flaherty et al. | |
| 2004/0254434 A1 | 12/2004 | Goodnow et al. | |
| 2004/0260233 A1 | 12/2004 | Garibotto et al. | |
| 2005/0004947 A1 | 1/2005 | Emlet et al. | |
| 2005/0022274 A1 | 1/2005 | Campbell et al. | |
| 2005/0041687 A1* | 2/2005 | Dowling et al. | 370/469 |
| 2005/0055398 A1* | 3/2005 | Olson et al. | 709/200 |
| 2005/0137653 A1 | 6/2005 | Friedman et al. | |
| 2005/0191716 A1* | 9/2005 | Surwit et al. | 435/13 |
| 2005/0192844 A1 | 9/2005 | Esler et al. | |
| 2006/0106941 A1* | 5/2006 | Singhal et al. | 709/238 |
| 2006/0129650 A1* | 6/2006 | Ho et al. | 709/207 |
| 2006/0167367 A1 | 7/2006 | Stanczak et al. | |
| 2006/0248398 A1 | 11/2006 | Neel et al. | |
| 2006/0279431 A1 | 12/2006 | Bakarania et al. | |
| 2007/0033074 A1 | 2/2007 | Nitzan et al. | |
| 2007/0048691 A1 | 3/2007 | Brown | |
| 2007/0055799 A1* | 3/2007 | Koehler et al. | 710/62 |
| 2007/0179352 A1 | 8/2007 | Randlov et al. | |
| 2007/0219432 A1 | 9/2007 | Thompson | |
| 2007/0258395 A1* | 11/2007 | Jollota et al. | 370/310 |
| 2007/0276197 A1 | 11/2007 | Harmon | |

FOREIGN PATENT DOCUMENTS

| | | |
|---|---|---|
| EP | 0 649 316 B1 | 12/2000 |
| EP | 1 194 864 A2 | 4/2002 |
| EP | 1 502 614 | 2/2005 |
| EP | 1 722 310 | 4/2005 |
| WO | WO9728736 | 2/1997 |
| WO | WO9935856 | 7/1999 |
| WO | WO0018449 | 2/2000 |
| WO | WO0072181 | 11/2000 |
| WO | WO0200111 | 1/2002 |
| WO | WO02078512 | 10/2002 |
| WO | WO03015838 | 2/2003 |
| WO | WO2004090661 | 10/2004 |
| WO | WO2005011249 | 2/2005 |
| WO | WO2005037095 | 4/2005 |
| WO | WO2005096206 | 10/2005 |
| WO | WO2005114534 | 12/2005 |
| WO | WO2005114535 | 12/2005 |
| WO | WO2006050485 | 2/2006 |
| WO | WO2006108858 | 10/2006 |
| WO | WO2006118763 | 11/2006 |
| WO | WO2007051139 | 5/2007 |
| WO | WO2007093482 | 8/2007 |
| WO | WO2008147567 | 12/2008 |

OTHER PUBLICATIONS

Cabri et al.; "*Agent-based Plug-and-Play Integration of Role-Enabled Medical Devices*", IEEE Computer Society, Aug. 2007, p. 111-121.

"*The HAVi Specification—Specification of the Home Audio/Video Interoperability (HAVi) Architecture,*" Nov. 19, 1998, pp. 1-409, Version 1.0 beta.

Hotchkiss et al.; "MD-Adapt a Proposed Architecture for Open-Source Medical Device Interoperability", 2007, IEEE Computer Society, Aug. 2007, pp. 167-169.

"CoPilot Health Management System Version 3.1," User's Guide, Mar. 2007, 230 pp., Art 10641 Rev. D, Abbott Diabetes Care, Inc.

"MediSense® Precision Link® Diabetes Data Management Software," User's Guide, May 2006, 58 pp., 116-412 Rev. AC, Abbott Diabetes Care, Inc.

Albisser, Michael A.; "A Graphical User Interface for Diabetes Management Than Integrates Glucose Prediction and Decision Support," Diabetes Technology & Therapeutics, 2005, pp. 264-273, vol. 7, No. 2.

Janssen et al., "Acensia® Winglucofacts® Professional Intelligent Diabetes Management Software Is an Effective Tool for the Management of Diabetes," Bayer HealthCare Clinical Summary Report, Jul. 2005, 10 pp.

Joshy et al.; "Diabetes Information Systems: A Rapidly Emerging Support for Diabetes Surveillance and Care," Diabetes Technology & Therapeutics, 2006, pp. 587-597, vol. 8, No. 5.

"OneTouch Diabetes Management Software," User Manual, 2006, 173 pp., v. 2.3.1, Lifescan, Inc.

"Getting Started, CareLink Personal Therapy Management Software for Diabetes," Brochure, 2007, 20 pp., Medtronic Minimed, Inc.

"Accu-Chek® Camit Pro Diabetes Management Software," User's Manual, 2005, 220 pp., v.2.1 and Addendum v. 2.4, Roche Diagnostics Corp.

"Accu-Chek® Compass Diabetes Care Software," User's Guide, 2005, 74 pp., Roche Diagnostics Corp.

"Accu-Chek® Diabetes Assistant," accessed with notional data and printed from www.diabetesassistant.com on Jan. 16, 2007, 20 pp., Roche Diagnostics Corp.

International Report and Written Opinion for PCT/EP2008/009861 issued by the European Patent Office on Apr. 21, 2009 (13 pages).

Schnayder, Victor et al., "Sensor Networks for Medical Care", Technical Report Harvard University, Jan. 1, 2005, pp. 1-14, vol. TR-08-05.

* cited by examiner

DYNAMIC COMMUNICATION STACK

FIELD OF THE INVENTION

The present invention relates to the communication between a resource and a computer. Specifically, the invention relates to protocols utilized to facilitate communication between a medical device and medical software.

DESCRIPTION OF THE RELATED ART

Protocols configured to facilitate the communication between a computer running a software application and a resource are known. Traditionally, in order for a computer to communicate with a resource, a software application running on the computer must be employed.

Generally, the software application includes static communication protocol stacks hard coded into the source code of the application that are used to communicate with a resource. In general, in order to facilitate communication between the resource and the computer, the user must instruct the software application as to the type of resource that is connected to the computer. Once the user has informed the software as to the type of resource that is connected to the computer, the application generally utilizes a specific communication protocol hard coded into the application code in order to facilitate communication.

SUMMARY OF THE INVENTION

An embodiment of the invention comprises a method of facilitating communication between a resource and a computer running a software program. The method includes the steps of establishing a link between the resource and the computer; ascertaining the type of resource linked with the computer, assembling a communication protocol based upon the type of device, and transferring data from the device to the computer based upon the assembled communication protocol.

The resource may be a medical device. The medical device may be a blood glucose meter, or the medical device may be an insulin pump.

In embodiments of the invention, the step of assembling a communication protocol includes the steps of locating the type of resource in a configuration information and assembling the communication protocol based upon instructions contained in the configuration information. Embodiments of the invention further comprise the step of downloading a new set of instructions into the configuration information if the type of resource is not included in the configuration information. The computer may be connected to the Internet, and the download of the new set of instructions may occur over the Internet. In embodiments of the invention, the download step occurs automatically. In other embodiments, the new set of instructions are downloaded from a transportable media.

In embodiments of the invention, the step of establishing a link occurs automatically. Embodiments of the invention further include the step of breaking the link between the device and the computer after downloading data from the resource to the computer. Embodiments of the invention may further include the step of transferring data from the computer to the resource. In addition, the communication protocol may be defined by a protocol stack including a plurality of blocks representative of communication blocks associated with an Open Systems Interconnection Basic Reference Model.

An embodiment of the invention comprises a method of transferring data between a computer and a resource. The method includes the steps of establishing a connection between the computer and the resource, determining the type of resource; selecting a communication protocol from a file stored on the computer that is based upon the type of resource connected to the computer, assembling a communication stack based upon the communication protocol, and transferring the data from the resource to the computer based upon the communication stack.

BRIEF DESCRIPTION OF THE FIGURES

The above-mentioned and other features and advantages of this invention, and the manner of attaining them, will become more apparent and the invention itself will be better understood by reference to the following description of embodiments of the invention taken in conjunction with the accompanying drawings, wherein.

Although the drawings represent embodiments of various features and components according to the present invention, the drawings are not necessarily to scale and certain features may be exaggerated in order to better illustrate and explain the present invention. The exemplifications set out herein illustrate embodiments of the invention, and such exemplifications are not to be construed as limiting the scope of the invention in any manner.

DETAILED DESCRIPTION OF EMBODIMENTS OF THE INVENTION

For the purposes of promoting an understanding of the principles of the invention, reference will now be made to the embodiments illustrated in the drawings, which are described below. It will nevertheless be understood that no limitation of the scope of the invention is thereby intended. The invention includes any alterations and further modifications in the illustrated device and described method and further applications of the principles of the invention, which would normally occur to one skilled in the art to which the invention relates. Moreover, the embodiments were selected for description to enable one of ordinary skill in the art to practice the invention.

Concepts described below may be further explained in one of more of the co-filed patent applications entitled HELP UTILITY FUNCTIONALITY AND ARCHITECTURE Ser. No. 11/999,906, METHOD AND SYSTEM FOR GRAPHICALLY INDICATING MULTIPLE DATA VALUES Ser. No. 11/999,853, SYSTEM AND METHOD FOR DATABASE INTEGRITY CHECKING Ser. No. 11/999,856, METHOD AND SYSTEM FOR DATA SOURCE AND MODIFICATION TRACKING Ser. No. 11/999,888, PATIENT-CENTRIC HEALTHCARE INFORMATION MAINTENANCE Ser. No. 11/999,874, EXPORT FILE FORMAT WITH MANIFEST FOR ENHANCED DATA TRANSFER Ser. No. 11/999,867, GRAPHIC ZOOM FUNCTIONALITY FOR A CUSTOM REPORT Ser. No. 11/999,932, METHOD AND SYSTEM FOR SELECTIVE MERGING OF PATIENT DATA Ser. No. 11/999,859, METHOD AND SYSTEM FOR PERSONAL MEDICAL DATA DATABASE MERGING Ser. No. 11/999,772, METHOD AND SYSTEM FOR WIRELESS DEVICE COMMUNICATION Ser. No. 11/999,879, METHOD AND SYSTEM FOR SETTING TIME BLOCKS Ser. No. 11/999,968, METHOD AND SYSTEM FOR ENHANCED DATA TRANSFER Ser. No. 11/999,911, COMMON EXTEN- SIBLE DATA EXCHANGE FORMAT Ser. No. 11/999,871, METHOD OF CLONING SERVER INSTALLATION TO A NETWORK CLIENT Ser. No. 11/999,876, METHOD AND SYSTEM FOR QUERYING A DATABASE Ser. No. 11/999,912, METHOD AND SYSTEM FOR EVENT BASED DATA COMPARISON Ser. No. 11/999,921, SYSTEM AND METHOD FOR REPORTING MEDICAL INFORMATION Ser. No. 11/999,878, METHOD AND SYSTEM FOR MERGING EXTENSIBLE DATA INTO A DATABASE USING GLOBALLY UNIQUE IDENTIFIERS Ser. No. 11/999,947, METHOD AND SYSTEM FOR ACTIVATING FEATURES AND FUNCTIONS OF A CONSOLIDATED SOFTWARE APPLICATION Ser. No. 11/999,880, METHOD AND SYSTEM FOR CONFIGURING A CONSOLIDATED SOFTWARE APPLICATION Ser. No. 11/999,894, METHOD AND SYSTEM FOR DATA SELECTION AND DISPLAY Ser. No. 11/999,896, METHOD AND SYSTEM FOR ASSOCIATING DATABASE CONTENT FOR SECURITY ENHANCEMENT Ser. No. 11/999,951, METHOD AND SYSTEM FOR CREATING REPORTS Ser. No. 11/999,851, METHOD AND SYSTEM FOR CREATING USER-DEFINED OUTPUTS Ser. No. 11/999,905, DATA DRIVEN COMMUNICATION PROTOCOL GRAMMAR Ser. No. 11/999,770, HEALTHCARE MANAGEMENT SYSTEM HAVING IMPROVED PRINTING OF DISPLAY SCREEN INFORMATION Ser. No. 11/999,855, and METHOD AND SYSTEM FOR MULTI-DEVICE COMMUNICATION Ser. No. 11/999,866, the entire disclosures of which are hereby expressly incorporated herein by reference. It should be understood that the concepts described below may relate to diabetes management software systems for tracking and analyzing health data, such as, for example, the ACCU-CHEK®360° product provided by Roche Diagnostics. However, the concepts described herein may also have applicability to apparatuses, methods, systems, and software in fields that are unrelated to healthcare. Furthermore, it should be understood that references in this patent application to devices, meters, monitors, pumps, or related terms are intended to encompass any currently existing or later developed apparatus that includes some or all of the features attributed to the referred to apparatus, including but not limited to the ACCU-CHEK® Active, ACCU-CHEK® Aviva, ACCU-CHEK® Compact, ACCU-CHEK® Compact Plus, ACCU-CHEK® Integra, ACCU-CHEK® Go, ACCU-CHEK® Performa, ACCU-CHEK® Spirit, ACCU-CHEK® D-Tron Plus, and ACCU-CHEK® Voicemate Plus, all provided by Roche Diagnostics or divisions thereof.

The terms "network," "local area network," "LAN," "wide area network," or "WAN" mean two or more computers which are connected in such a manner that messages may be transmitted between the computers. In such computer networks, typically one or more computers operate as a "server", a computer with large storage devices such as hard disk drives and communication hardware to operate peripheral devices such as printers or modems. Other computers, termed "workstations", provide a user interface so that users of computer networks can access the network resources, such as shared data files, common peripheral devices, and inter-workstation communication. The computers have at least one processor for executing machine instructions, and memory for storing instructions and other information. Many combinations of processing circuitry and information storing equipment are known by those of ordinary skill in these arts. A processor may be a microprocessor, a digital signal processor ("DSP"), a central processing unit ("CPU"), or other circuit or equivalent capable of interpreting instructions or performing logical actions on information. Memory includes both volatile and non-volatile memory, including temporary and cache, in electronic, magnetic, optical, printed, or other format used to store information. Users activate computer programs or network resources to create "processes" which include both the general operation of the computer program along with specific operating characteristics determined by input variables and its environment.

As used herein the term "Common Data Format" (CDF) refers to a specification that describes the structure of data used to exchange data between components of a system and between the system and other medical information systems. CDF also refers to a file that conforms to the above described specification. CDF 300 utilizes Extensible Markup Language (XML) which is a specification developed by the W3C that defines a markup language used to describe the structure of data in a platform-independent way. However, the present CDF 300 is not intended to be limited to instances including XML. An XML Schema is a specification developed by the W3C that defines an XML language used to define and document the structure of an XML document and to impose constraints on the content of the XML document. A XML Schema Definition (XSD) is an instance of the XML Schema specification that defines a specific structure for XML documents.

The terms Extract, Transform and Load, abbreviated herein as "ETL" are discussed in the context of data warehousing. ETL is the process of extracting data from a system then transforming and loading that data into another system.

Figure 1:
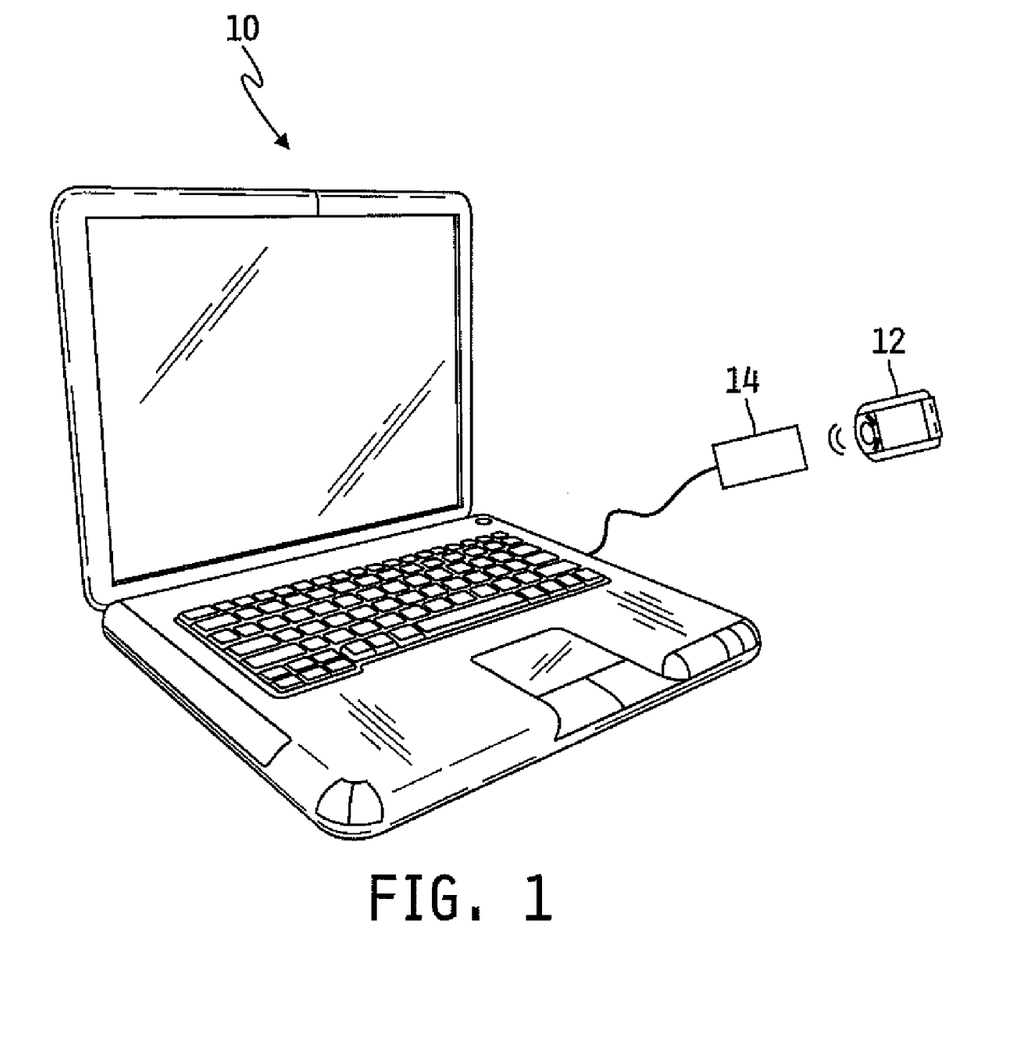
FIG. 1 depicts a computer and resource representing an embodiment of the present invention.

With the above general understanding, FIG. 1 depicts a computer, generally indicated by numeral 10, and a resource, generally indicated by numeral 12. Computer 10 may be any type of computer capable of running a software application. In the depicted embodiment, computer 10 is a laptop computer. In addition, computer 10 includes transceiver 14. Transceiver 14 may be connected to computer 10 in any suitable manner, such as through a USB connection, for example. In embodiments, transceiver 14 may be integrated into computer 10.

For purposes of the present example, computer 10 includes a hard drive (not shown) capable of storing data in a conventional manner. In addition, computer 10 is capable of running software loaded into the memory of the hard drive, and computer 10 may also run software from a server. In embodiments, the software installed on computer 10 may be ACCU-CHEK® 360° software manufactured by Roche Diagnostics, which may be loaded into the memory of computer 10 in any suitable manner.

Resource 12 may be any suitable medical device capable of communicating with the software stored in the memory of computer 10, such as a blood glucose meter or an insulin pump, for example, which are generally known. Resource 12 may further include any suitable information management device, such as a personal data assistant, for example. An additional example of an information management device is the Accu-Chek® Pocket Compass® manufactured by Roche Diagnostics.

Resource 12 includes a dynamic memory capable of allowing the resource 12 to store and save various types of data thereon. For example, in embodiments in which resource 12 is a blood glucose meter, the resource 12 can measure the blood glucose values of a patient with diabetes and store the measured values in a database.

Traditionally, in order to facilitate communication between computer 10 and resource 12, a user is required to instruct computer 10 as to the type of resource 12 connected with computer 10. Once the user has selected the type of resource 12, the software application being run by computer 10 retrieves a communication protocol specific to the type of resource 12 that resides within the source code of the software. The computer 10 utilizes this communication protocol to communicate and interact with the resource 12. Accordingly, the software application must include a plurality of communication protocols included in its source code. Furthermore, a new communication protocol must be added to the source code of the application in a suitable manner every time that the software is updated to communicate with a new resource 12.

Figure 2:
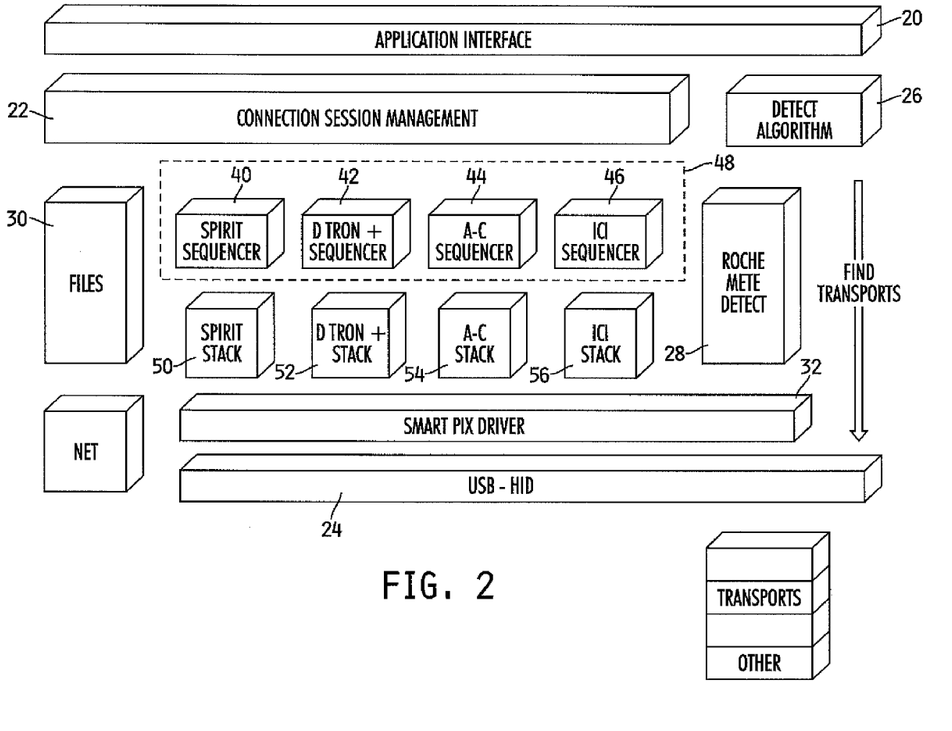
FIG. 2 depicts a schematic of a communication protocol representing an embodiment of the present invention.

FIG. 2 depicts a schematic representing the function of the software run on computer 10 during the communication between the computer 10 and the resource 12. In the schematic, block 20 indicates the application interface that allows the software to receive and communicate with resource 12. As should be understood by one of ordinary skill in the art, the application interface generally corresponds to the type of operating system being utilized by the computer 10.

Numeral 22 generally indicates a block representing the connection session management function of the software. The connection session management block 22 represents the interaction between the application software and the computer 10 itself. The connection session management 22 may be accomplished in any suitable manner.

Numeral 24 generally indicates a block representing the physical connection of a Human Interface Device (HID) through a Universal Serial Bus (USB) in computer 10. In the present example, the HID may be transceiver 14. In other embodiments of the invention, the HID may be a resource 12 that plugs directly into a USB port included in computer 10.

Referring still to FIG. 2, numeral 26 generally indicates a block representing a detect algorithm. In the present example, detect algorithm 26 is configured to detect when a resource 12 is connected to computer 10, and when computer 10 begins communicating with resource 12 through the USB-HID 24.

In the present example, numeral 28 indicates a block representing a detect resource type algorithm. The detect resource type algorithm 28 determines the type of resource communicating with the computer 10. The determination of the resource 12 may be accomplished in any suitable manner. For example, the resource 12 may send an identifier to the computer 10, and the detect resource type algorithm 28 may utilize the identifier to determine the type of resource 12 communicating with computer 10. In other embodiments, the resource 12 may send a serial number or a model number, which may be used by the detect resource type algorithm to ascertain the type of resource 12. For example, the model number or serial number may include, as a portion thereof, an alphanumeric string capable of identifying the resource 12. After receiving the serial number or model number, the detect resource type algorithm 28 may parse the received number in order to extract the portion that is relevant to the determination of the type of resource 12 and then compare this relevant portion to identification information utilized by the algorithm 28.

Referring still to FIG. 2, numeral 30 indicates a block representing a file format converter. File, as used herein, includes content, data and information stored on both the computer 10 and the resource 12 in any manner. File format converter 30 is capable of altering the format of files in a suitable manner. For example, file format converter 30 may take a file of a first format received from resource 12 and convert the file into a second format for utilization by the software application on computer 10.

Numeral 32 indicates a block representing a driver. In the present example, driver 32 is a Smart Pix Driver configured to drive a Smart Pix device manufactured by Roche Diagnostics. The Smart Pix device is capable of being connected to a computer 10 via a USB port and assists in the transfer of data from blood glucose meters and insulin pumps to the computer 10. In the present example, transceiver 14 may be a Smart Pix device.

Numerals 40, 42, 44, 46 indicate blocks representing various sequencers. Specifically, numeral 40 indicates a Spirit Sequencer. Spirit is a type of insulin pump produced by Roche Diagnostics. Numeral 42 indicates a D-Tron+ Sequencer. D-Tron+ is another type of insulin pump produced by Roche Diagnostics. Numeral 44 indicates an A-C Sequencer. Roche Diagnostics manufactures blood glucose meters operating under a control method dubbed Active-Compact. Numeral 46 indicates an ICI Sequencer. Roche Diagnostics manufactures blood glucose meters operating under a control method dubbed ICI. Numeral 48 represents a configuration information. In embodiments of the invention, the Sequencers 40, 42, 44, 46 may be stored in a single configuration information file 48, as depicted. In embodiments of the invention, the Sequencers 40, 42, 44, 46 may be distinct files.

As shown in FIG. 2, numerals 50, 52, 54, 56 indicate blocks representing various stacks. Each one of the stacks 50, 52, 54, 56 corresponds to one of the sequencers 40, 42, 44, 46. For example, sprit stack 50 corresponds to the spirit sequencer 40. Similarly, D-Tron+ stack 52 corresponds to the D-Tron+ Sequencer 42. This relationship holds true for the A-C Stack 54 and ICI Stack 56 and the corresponding A-C Sequencer 44 and ICI Sequencer 46, respectively.

It should be noted that the stacks 50, 52, 54, 56 are not permanently resident in the memory of computer 10. Instead, the stacks 50, 52, 54, 56 are dynamically created by the software application, as necessary. Specifically, the Sequencers 40, 42, 44, 46 each contain information that allows the Stack 50, 52, 54, 56 corresponding to each Sequencer 40, 42, 44, 46 to be constructed when needed. For example, the Spirit Sequencer 40 includes instructions allowing the software to construct the Spirit Stack 50 in order to allow computer 10 to communicate with a Spirit Insulin Pump. Once the Stacks 50, 52, 54, 56 have been created, the Stacks 50, 52, 54, 56 provide a communication protocol allowing the software application to communicate with the resource 12. In general, the Stacks 50, 52, 54, 56 may be considered as including a plurality of layers similar to the Open Systems Interconnection (OSI) model architecture. It should be noted that the Stacks 50, 52, 54, 56 do not necessarily incorporate all seven layers of the OSI architecture, but may instead incorporate some sub-set of the seven layers corresponding to the traditional OSI architecture. In addition, in embodiments, the corresponding stacks may deviate from the OSI architecture. For example, communication under the Bluetooth® model comprises layers representing Radio, Baseband, Link Manager Protocol (LMP), Host Controller Interface (HCI), Logical Link Control and Adaptation Protocol (L2CAP), RFCOMM and Service Discovery Protocol (SDP).

In operation, a resource 12 first communicates with computer 10 via a USB port in the computer 10. As explained above, resource 12 may be connected directly to computer 10 via the USB, or a transceiver 14 may be plugged into the USB port on the computer 10 and the resource 12 may communicate with the transceiver 14. The USB port on the computer 10 that connects to resource 12 represents the USB-HID block 24. It should be noted that generally, device driver 32 corresponds to transceiver 14, and driver 32 allows computer 10 to communicate with the resource 12.

Once the computer 10 first begins communication with resource 12, detect algorithm block 26 detects the presence of the resource 12. Further details regarding detection of resource 12 may be provided in co-filed patent application entitled METHOD FOR MULITPORT SCANNING, the entire disclosure of which is expressly incorporated herein by reference. Upon determining that a resource 12 is communicating with computer 10 via detect algorithm block 26, the software application triggers the detect resource type algorithm 28. Detect resource type algorithm 28 determines the type of resource 12 connected to computer 10 by building protocol stacks dynamically to determine the resource 12 connected. It should be noted that at this time, only minimal file information is sent from the resource 12 to the computer 10, and thus minimal information is forwarded to the detect resource type algorithm 28. After receiving the information, the detect resource type algorithm 28 processes the information passed from resource 12 to computer 10 and determines the type of resource 12 that is communicating with the computer 10.

It should be noted that in embodiments, if a Sequencer is not found that corresponds to the type of resource 12 connected to computer 10, the software may attempt to locate additional information regarding the type of resource 12 connected to the computer 10 by utilizing the Internet, if available. For example, the software may connect to a server having a known IP address and communicate with the server in order to determine the type of resource 12. If the server includes information relating to the type of resource 12, computer 10 may download that information for future utilization by the detect resource type algorithm 28.

Once the detect resource type algorithm 28 has determined the type of resource 12, the software locates the Sequencer 40, 42, 44, 46 that corresponds to the type of resource 12 connected to computer 10. It should be noted that the Sequencers 40, 42, 44, 46 may represent multiple files or may be stored in a single file, such as a configuration information file.

In the event that the Sequencers 40, 42, 44, 46 present within the software do not correspond to the type of resource 12 connected to computer 10, the software may utilize the Internet in an attempt to locate an update. For example, the computer 10 may connect to a remote server via the Internet and provide the remote server with the type of resource 12. If the remote server includes information relating to the specified type of resource 12, the server may provide an appropriate Sequencer file to the software. In embodiments, where necessary, the server may provide an updated file including all of the known sequencers for incorporation into the software application, thereby presenting the software application from having to communicate with the remote server the next time a similar resource 12 is connected to the computer 10.

Once the appropriate Sequencer 40, 42, 44, 46 has been selected, the sequencer is added to the communication stack. The sequencers generally send commands from the computer 10 to the resource 12. The commands generally instruct the resource 12 to send information, such as data, to the computer 10. In embodiments of the invention, the sequencer 40, 42, 44, 46 receives the information and sends the information to a client, such as a user interface. For example, if resource 12 is a Spirit Insulin Pump, Spirit Sequencer 40 will be selected. Spirit Sequencer 40 will provide the computer 10 with instructions as to how to retrieve data from the Spirit Insulin Pump 12.

In the present example, Spirit Stack 50 includes four elements of a traditional 7 layer Open Systems Interconnection Basic Reference Model: a transport layer, a datalink layer, an application layer and a sequencer. Similarly, in the present example, the D-Tron+ Stack 52 includes a transport Layer, a datalink layer, an application layer and sequencer. In the present example, the A-C Stack 54 and the ICI Stack 56 each includes three elements: a transport layer, an application layer and a sequencer.

Once the appropriate stack has been constructed by the software application, the software utilizes the constructed stack to allow communication between the computer 10 and the resource 12. Accordingly, in embodiments, if the data is stored on the resource 12, the data may be downloaded onto the computer 10 automatically. In the present example, the software application utilizes the stack 50 along with the USB-HID block 24, the Driver block 32, connection management 22, and application interface 20 to connect computer 10 with resource 12 in order to download and interpret the data stored on the resource 12. In embodiments, if necessary, a user may interact with the computer 10 as the computer 10 downloads information from the resource 12. Computer 10 may also upload information or data onto resource 12. Once the interaction between the computer 10 and the resource 12 has been completed, the appropriate stack may be removed from the memory of the computer 10. At a later time, the connection of a resource 12 to the computer 10 allows another stack to be constructed in accordance with the process set forth above, thereby allowing the resource 12 to be connected to the computer 10. Once the communication between the resource 12 and computer 10 has ceased, the Stack may be deleted from the memory of the computer 10 and rebuilt in further sessions, as necessary.

Although the software is described herein for operation on a computer (e.g., desktop, laptop or tablet), it should be understood that the principles of the invention may be embodied in software for operation on various devices, including but not limited to personal digital assistants ("PDAs"), infusion pumps, blood glucose meters, cellular phones, or integrated devices including a glucose measurement engine and a PDA or cellular device.

The invention is described herein with reference to healthcare data management software, and more particularly, with reference to diabetes management software, although the invention may be applied, generally, to data management systems in fields unrelated to healthcare management.

While the invention is described herein with reference to medical devices, and more particularly, with reference to diabetes management devices, the invention is applicable to any data obtained from any device.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method of facilitating communication between a resource and a computer running a software program comprising the steps of:

establishing a link between the resource and the computer;

ascertaining with a detection algorithm stored on the computer the type of resource linked with the computer;

locating configuration information corresponding to the type of resource linked with the computer, the configuration information comprising a plurality of machine-executable instructions;

wherein the computer dynamically creates a communication protocol stack comprising a plurality of communication layers, by executing at least one of the machine-executable instructions of the configuration information to incorporate at least two of the communication layers into the communication protocol stack, the at least two communication layers including an application layer;

transferring data from the resource to the computer based upon the dynamically created communication protocol stack; and removing the communication protocol stack entirely from the memory of the computing device upon the completion of the interaction between the portable medical device and the computing device.

2. The method as set forth in claim 1 wherein the resource is a medical device.

3. The method as set forth in claim 2 wherein the medical device is a blood glucose meter.

4. The method as set forth in claim 2 wherein the medical device is an insulin pump.

5. The method as set forth in claim 1 wherein the step of locating the configuration information comprises downloading the configuration information corresponding to the type of resource linked with the computer.

6. The method as set forth in claim 5 wherein the computer is connected to the Internet and the download of the configuration information occurs over the Internet.

7. The method as set forth in claim 6 wherein the download step occurs automatically.

8. The method as set forth in claim 1 wherein the step of establishing a link occurs wirelessly.

9. The method as set forth in claim 1 further comprising the step of breaking the link between the resource and the computer after transferring data from the resource to the computer.

10. The method as set forth in claim 1 further comprising the step of transferring data from the computer to the resource.

11. The method as set forth in claim 1 wherein the plurality of communication layers of the communication protocol stack is defined by a plurality of blocks representative of communication blocks associated with an Open Systems Interconnection Basic Reference Model.

12. The method as set forth in claim 1 wherein the plurality of machine-executable instructions of the configuration information includes a plurality of blocks representative of at least one of the plurality of communication layers of the communication protocol stack needed for communication with the resource.

13. A method of transferring data between a computer and a resource comprising the steps of:

establishing a connection between the computer and the resource;

using a detection algorithm stored on the computer to determine the type of resource;

selecting a sequencer from a file stored on the computer that is based upon the type of resource connected to the computer, the sequencer comprising a plurality of computer-executable instructions;

wherein the computer dynamically creates a communication protocol stack including a plurality of task layers based upon the sequencer by executing at least one of the computer-executable instructions of the sequencer to incorporate at least two of the plurality of task layers into the communication protocol stack, the at least two task layers including an application layer;

transferring the data from the resource to the computer based upon the communication protocol stack; and removing the communication protocol stack entirely from the memory of the computing device upon the completion of the interaction between the portable medical device and the computing device.

14. The method as set forth in claim 13 further comprising the step of transferring data from the computer to the resource.

15. The method as set forth in claim 13 further comprising the step of transmitting a set of identification information from the resource to the computer.

16. The method as set forth in claim 15 wherein the set of identification information includes a model number.

17. The method as set forth in claim 15 wherein the computer determines the type of resource based upon the set identification information.

18. The method as set forth in claim 13 wherein the resource is a medical device.

19. The method as set forth in claim 18 wherein the device is a blood glucose meter.

20. The method as set forth in claim 18 wherein the device is an insulin pump.

21. The method as set forth in claim 13 wherein the connection between the computer and the resource is a wireless connection.

22. The method as set forth in claim 13 wherein the communication protocol stack is based upon an Open Systems Interconnection Basic Reference Model.

23. The method as set forth in claim 13 further comprising the step of downloading the sequencer from a server if the file stored on the computer does not include a sequencer corresponding to the type of resource connected to the computer.

24. The method as set forth in claim 23 wherein the downloading step occurs automatically and over the Internet.

25. The method as set forth in claim 13 wherein the resource is an information management device.

26. A method of facilitating communication of patient medical information, stored on a portable medical device, with a computing device running a healthcare data management software application and having a memory, the method comprising the steps of:

establishing a link between the portable medical device and the computing device, wherein the link is established by a transceiver;

transmitting an alphanumeric string identifier from the portable medical device to the computing device;

initiating a detection algorithm, wherein the detection algorithm signals the healthcare data management software application that a portable medical device is linked to the computing device;

initiating a detection resource algorithm of the computing device, wherein the detection resource algorithm utilizes the alphanumeric string identifier to determine the type of portable medical device linked to the computing device, and further wherein the detection resource algorithm identifies sequencer information stored in the memory of the computing device and associated with the type of portable medical device;

the computing device dynamically creating, in the memory of the computing device, a communication protocol stack comprising a plurality of communication layers based on the sequencer information associated with the identified portable medical device by executing at least one of the computer-executable instructions of the sequencer information to incorporate at least two of the communication layers into the communication protocol stack, the at least two communication layers including an application layer, wherein the communication protocol stack instructs the healthcare data management software application to send a plurality of commands to the portable medical device instructing the portable medical device to communicate patient medical information to the computing device;

transferring the patient medical information from the portable medical device to the healthcare data management software application based upon the created communication protocol stack;

converting the patient medical information stored on the portable medical device from a first file format to a second file format with a file format converter, wherein the second file format is readable by the healthcare data management software; and removing the communication protocol stack entirely from the memory of the computing device upon the completion of the interaction between the portable medical device and the computing device.

* * * * *